United States Patent
Sato et al.

(10) Patent No.: US 7,921,991 B2
(45) Date of Patent: Apr. 12, 2011

(54) HOUSING CONTAINER FOR IMPLANT FIXTURE

(75) Inventors: Kimihiko Sato, Itabashi-ku (JP); Kinya Nihei, Itabashi-ku (JP); Makoto Michiaki, Itabashi-ku (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 12/730,391

(22) Filed: Mar. 24, 2010

(65) Prior Publication Data

US 2010/0243485 A1 Sep. 30, 2010

(30) Foreign Application Priority Data

Mar. 24, 2009 (JP) ................................. 2009-072193

(51) Int. Cl.
*A61C 19/02* (2006.01)
*B65D 83/10* (2006.01)
(52) U.S. Cl. ............ 206/63.5; 206/368; 433/9; 433/173
(58) Field of Classification Search ................. 206/63.5, 206/368, 369, 339, 453, 493, 521, 583, 586, 206/588; 433/8, 9, 173, 229
See application file for complete search history.

(56) References Cited

U.S. PATENT DOCUMENTS

| | | | | |
|---|---|---|---|---|
| 2,136,352 A | * | 11/1938 | Hommedieu | 206/63.5 |
| 5,062,800 A | * | 11/1991 | Niznick | 206/368 |
| 5,368,160 A | * | 11/1994 | Leuschen et al. | 206/339 |
| 6,217,332 B1 | * | 4/2001 | Kumar | 433/173 |
| 6,309,220 B1 | * | 10/2001 | Gittleman | 433/173 |
| 2008/0217190 A1 | * | 9/2008 | Matsushige et al. | 206/63.5 |

* cited by examiner

*Primary Examiner* — Luan K Bui
(74) *Attorney, Agent, or Firm* — Oblon, Spivak, McClelland, Maier & Neustadt, L.L.P.

(57) ABSTRACT

To minimize titanium materials and accurately and easily fix a dental implant fixture, a housing container includes a glass housing main body, a resin cap, and a resin implant fixture holding member, the cap includes a press part at an inner surface, the implant fixture holding member fits into the bottom side of the housing main body, the implant fixture holding member has, at an upper surface side, three or more groove parts formed radially from a center to an end side, and titanium plate-like guide parts which include, at the center side, projected portions slightly projecting from the upper surface, and include, at the radial end side, erected portions extending up to at least equal to or more than ⅓ of a height from a tip of the dental implant fixture to erect around an outer peripheral surface of the dental implant fixture are inserted in the groove parts.

9 Claims, 7 Drawing Sheets

HOUSING CONTAINER FOR IMPLANT FIXTURE

BACKGROUND OF THE INVENTION

1. Field of the Invention

The present invention relates to a housing container for an implant fixture to house a dental implant fixture used in a dental implant treatment.

2. Description of the Conventional Art

One of recently prevailing dental prosthesis treatments is a dental implant treatment in which a dental implant fixture made of titanium or a titanium alloy having excellent biocompatibility is embedded in a jawbone at a lost tooth position, and is used instead of a natural dental root through a direct bond with the bone (osseointegration). The dental implant fixture used in the dental implant treatment is configured separately from an abutment for fixing a dental prosthesis, or is configured integrally with the abutment.

The dental implant fixture is strongly required to be sanitary because of being embedded in a jawbone. Thus, a housing container for an implant fixture to house a dental implant fixture is also strongly required to have high sealability to secure a sterilized condition.

As for a housing container for an implant fixture capable of securing a sterilized condition and having high sealability, for example, Japanese Patent Application Laid-Open No. 2008-284145 discloses a housing container in which a housing main body is made of a titanium material, which is a same material as that of the dental implant fixture, in order to make impurities hardly adhere to the dental implant fixture. However, since this housing container for an implant fixture has the housing main body made of a titanium material, there is a problem of wasting titanium resources when considering a fact that the housing container for an implant fixture is a disposable.

Japanese translation of PCT Publication No. 2000-512194, Japanese Translation of PCT Publication No. 2004-526530, and Japanese Patent Application Laid-Open No. 2008-125982, for example, disclose housing containers for an implant fixture to solve the aforementioned problem. The housing container for an implant fixture has a housing main body made of a resin, and houses a dental implant fixture by engaging a fixture mount in advance with an intraoral side end portion of a dental implant fixture and hanging the dental implant fixture with the fixture mount. In this housing container for an implant fixture, the dental implant fixture is hung, and an outer surface of the dental implant fixture is not in contact with an inner surface of the housing main body. Thus, the housing main body has advantages that it does not need to be made of titanium, and the dental implant fixture is hardly damaged during conveyance. However, there are problems that this housing container for an implant fixture needs many parts for hanging the dental implant fixture and in addition, since the fixture mount need to be removed after the dental implant fixture is embedded, it takes much time and work.

Japanese Patent Application Laid-Open No. 2004-243127 and Japanese Translation of PCT Publication No. 2004-510541, for example, disclose housing containers for an implant fixture to solve the aforementioned problems. The housing container for an implant fixture includes a holder part in a housing main body instead of a fixture mount, and houses a dental implant fixture by holding an intraoral side end portion of the dental implant fixture with the holder part. This housing container for an implant fixture has an advantage that it does not use a fixture mount, and thus the dental implant fixture can be directly taken out by a tool. However, there is a problem that, since holder part holds the intraoral side end portion of the dental implant fixture, when the dental implant fixture is taken out from the holder part, an outer surface of the dental implant fixture could be damaged because of scraping against the holder part. Further, the housing container for an implant fixture has a problem that, if an outer diameter of a collar part provided at the intraoral side end portion of the dental implant fixture is not larger than an outer diameter of an embedding portion, the holder part cannot hold the dental implant fixture, and thus the housing container for an implant fixture cannot house a dental implant fixture having the outer diameter of the collar part which is equal to the outer diameter of the embedding portion.

SUMMARY OF THE INVENTION

Problem to be Solved by the Invention

In view of the problems mentioned above, the present invention is directed to a housing container for housing a dental implant fixture, which is made with a minimum titanium material for not wasting titanium resources, can accurately and easily fix various kinds of dental implant fixtures, and does not damage the housed dental implant fixture when the dental implant fixture is conveyed or taken out.

Means for Solving the Problem

Present inventors carried out earnest works to solve the aforementioned problems, and as a result, they found out the followings to complete the present invention. A housing container for an implant fixture includes a housing main body made of glass or a resin, a cap made of a resin, and an implant fixture holding member made of a resin. The housing main body houses a dental implant fixture having an engagement hole in the intraoral side for engagement with a tool for embedding the dental implant fixture in a jawbone. The cap seals an upper part of the housing main body and includes a press part at an inner surface, where the press part is inserted into the engagement hole of the dental implant fixture to be in contact with the dental implant fixture, and/or is in contact with an upper surface on the intraoral side of the dental implant fixture. The implant fixture holding member is fitted into the bottom part side in the housing main body. In this housing container for an implant fixture, the implant fixture holding member includes three or more groove parts on the upper surface side, and the groove parts are formed radially from a part around a center to an end side of the implant fixture holding member. Further, a plate-like guide part made of titanium or a titanium alloy is inserted into each of the groove parts. The plate-like guide part has, at the center side thereof, a projected portion slightly projecting from the upper surface of the implant fixture holding member. The plate-like guide part has, at the radial end side thereof, an erected portion extending up to at least equal to or more than ⅓ of a height from tip of the dental implant fixture, and erecting around an outer peripheral surface of the dental implant fixture. In this housing container for an implant fixture configured as mentioned above, titanium materials are used only for the plate-like guide parts, which include the projected portions slightly projecting from the upper surface of the implant fixture holding member and the erected portions. The slightly projected portions are in direct contact with a portion of the dental implant fixture which is to be embedded in an alveolar ridge, and the erected portions could be in contact with a portion of the dental implant fixture which is to be embedded in an alveolar ridge. Thus, the housing container for an implant fixture can prevent wasting of titanium resources. Further, the housing container for an implant fixture holds and fixes the dental implant fixture with both the press part and the portion configured at the center side in the plate-guide parts to slightly project from the upper surface of the implant fixture holding member. Thus, the housing container for an implant fixture can accurately and easily positions and fixes various kinds of dental implant fixtures. In addition, the portions configures at the radial end side in the plate-like guide parts to extend up to at least equal to or more than ⅓ of the height from the tip of the dental implant fixture and to erect around the outer peripheral surface of the dental implant fixture, surround the outer peripheral surface of the dental implant fixture. Thus, the positioned and fixed dental implant fixture does not move greatly in the housing main body during conveyance, so that the dental implant fixture is not damaged. Furthermore, after the housing container for a dental implant fixture being opened, the positioned and fixed dental implant fixture can be easily taken out directly by a tool for embedding the dental implant fixture into a jawbone without contacting other portions in the housing main body.

According to an aspect of the present invention, a housing container for an implant fixture includes a housing main body made of glass or a resin, to house a dental implant fixture having an engagement hole in the intraoral side for engagement with a tool for embedding the dental implant fixture in a jawbone, a cap made of a resin to seal an upper part of the housing main body and provided with a press part at an inner surface, the press part being inserted into the engagement hole of the dental implant fixture to be in contact with the dental implant fixture and/or being in contact with an upper surface on the intraoral side of the dental implant fixture, and an implant fixture holding member made of a resin and fitted into the bottom part side in the housing main body, wherein the implant fixture holding member includes three or more groove parts on the upper surface side thereof, the groove parts are formed radially from a part around a center to an end side of the implant fixture holding member, a plate-like guide part made of titanium or a titanium alloy is inserted into each of these groove parts, the plate-like guide part has, at the center side thereof, a projected portion slightly projecting from an upper surface of the implant fixture holding member, and the plate-like guide part has, at the radial end side thereof, an erected portion extending up to at least equal to or more than ⅓ of a height from a tip of the dental implant fixture and erecting around an outer peripheral surface of the dental implant fixture.

As for the housing container for an implant fixture mentioned above, when the housing main body is formed in a cylindrical shape having an open upper end and an open lower end, the housing main body can house various kinds of dental implant fixtures having different lengths by fitting the implant fixture holding member into the housing main body according to the length of the dental implant fixture to be housed. So, it is preferable. Further, when the housing main body is formed in a container shape having a closed lower end, the housing container for an implant fixture can have higher sealability, so it is preferable.

The housing container for an implant fixture can also have a configuration that at least two adjacent groove parts communicate with each other at the radial center sides to form a V shape, a plate-like guide part inserted into the groove parts is U shape and an opening side of the plate-like guide part is upward, a bottom part of the plate-like guide part being the opposite side to the opening side is bent in a V shape at a center part thereof. In addition, the housing container for an implant fixture can also have a configuration that a groove part is formed in a cross shape intersecting at a center axis on the upper surface side of the implant fixture holding member, and plate-like guide parts having a U shape are arranged so as to intersect with each other by a halving joint and inserted into the groove part. According to these configurations, since the number of the plate-like guide parts to be inserted into the groove parts can be reduced, an operation for inserting the plate-like guide parts into the groove parts can be made easy, so it is preferable.

EFFECT OF THE INVENTION

According to the housing container for an implant fixture, titanium materials are used only for the plate-like guide parts having the projected portions slightly projecting from the upper surface of the implant fixture holding member, which are in direct contact with a portion of the dental implant fixture embedded in an alveolar ridge, and having the erected portions which could be in contact with a portion of the dental implant fixture embedded in the alveolar ridge. Thus, a use of titanium materials is limited to the minimum and the present invention can prevent wasting of titanium resources. Further, the housing container for an implant fixture holds and fixes the dental implant fixture with both the press part and the projected portions at the center side in the plate-guide parts slightly projecting from the upper surface of the implant fixture holding member instead of fixing the dental implant fixture with an outer peripheral surface thereof or with a fixture mount. Thus, the housing container for an implant fixture can accurately and easily fix various kinds of dental implant fixtures. In addition, the erected portions at the radial end side in the plate-like guide parts extend up to at least equal to or more than ⅓ of the height from the tip of the dental implant fixture, and erect around the outer peripheral surface of the dental implant fixture so as to surround the outer peripheral surface of the dental implant fixture. Thus, even when a big impact is applied to the housing container for a dental implant fixture during conveyance, the fixed dental implant fixture does not move greatly in the housing main body, so that the dental implant fixture is not damaged. Furthermore, after the housing container for a dental implant fixture being opened, the dental implant fixture can be easily taken out directly by a tool for embedding the dental implant fixture into a jawbone being engaged with the engagement hole provided in the intraoral side of the dental implant fixture, without contacting other portions in the housing main body.

As for the housing container for an implant fixture, when the housing main body is formed in a cylindrical shape having an open upper end and an open lower end, the housing main body can house various kinds of dental implant fixtures having different lengths by fitting the implant fixture holding member into the housing main body according to the length of the dental implant fixture to be housed. So, it is preferable. Further, when the housing main body is formed in a container shape having a closed lower end, the housing container for an implant fixture can have higher sealability, so it is preferable.

The housing container for an implant fixture can also have a configuration that at least two adjacent groove parts communicate with each other at the radial center sides to form a V shape, a plate-like guide part inserted into the groove part is a U shape and an opening side of the plate-like guide part is upward, a bottom part of the plate-like guide part being opposite side to the opening side is bent in a V shape at a center part thereof, and a configuration that a groove part is formed in a cross shape intersecting at a center axis on the upper surface side of the implant fixture holding member, and plate-like guide parts having a U shape are arranged so as to intersect with each other by a halving joint and inserted into the groove part. According to these configurations, since the number of the plate-like guide parts to be inserted into the groove parts can be reduced, an operation for inserting the plate-like guide parts into the groove parts can be made easy, so it is preferable.

DETAILED DESCRIPTION OF PREFERRED EMBODIMENT

Figure 1:
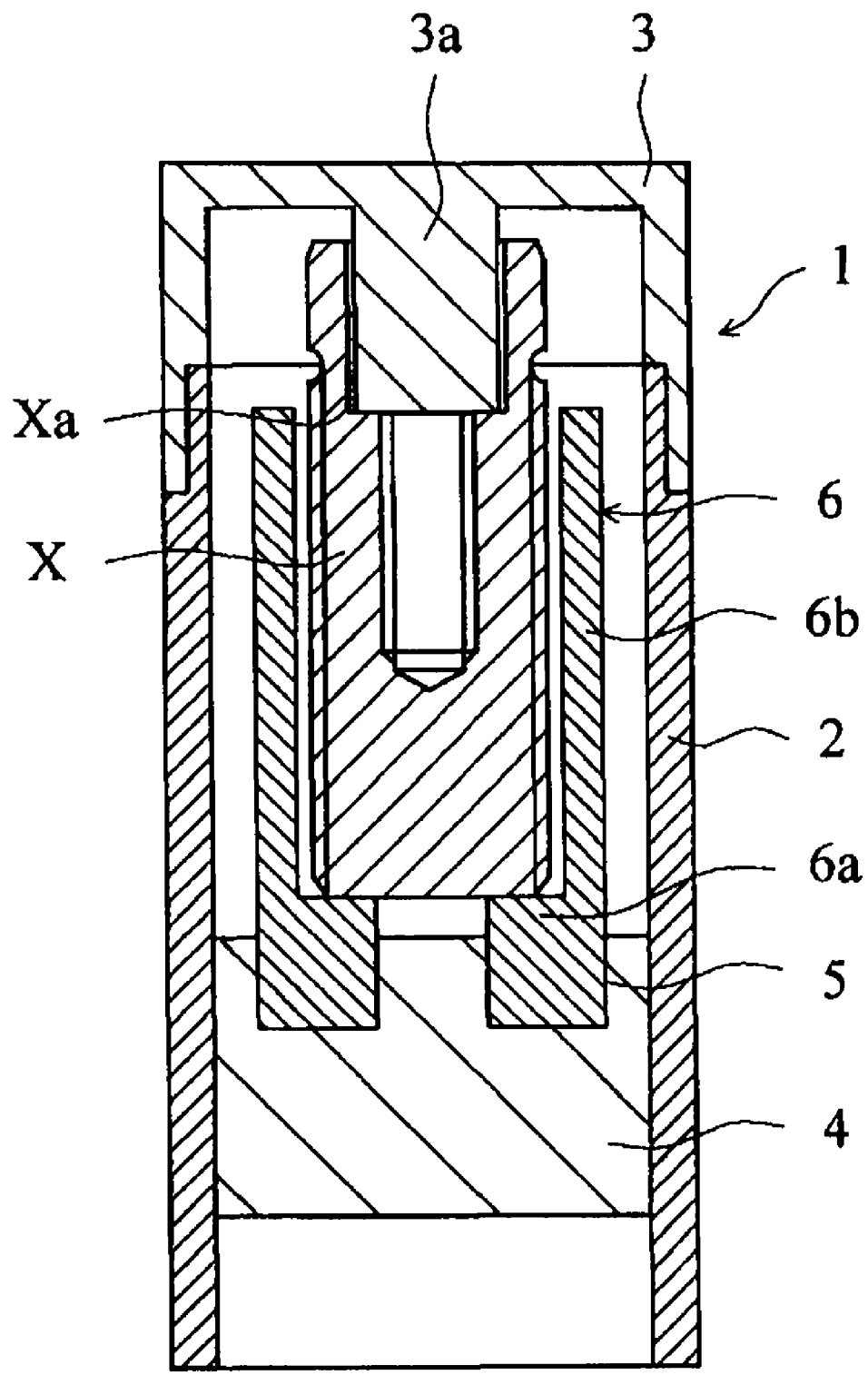
FIG. 1 is a longitudinal sectional view for illustrating one example of a housing container for an implant fixture according to the present invention.

In these drawings, a dental implant fixture X includes an engagement hole Xa on the intraoral side, and the engagement hole Xa engages with a tool for embedding the dental implant fixture X into a jawbone. The dental implant fixture X is taken out from a housing container 1 for an implant fixture according to the present invention as mentioned below by a taking-out tool and the like, after opening of the housing container 1 for an implant fixture. The dental implant fixture X is configured separately from an abutment for fixing a dental prosthesis, or is configured integrally with the abutment.

The housing container 1 for an implant fixture according to the present invention houses the dental implant fixture X. The housing container 1 for an implant fixture includes a housing main body 2, a cap 3, an implant fixture holding member 4, and a plate-like guide part 6.

The housing main body 2 is a base body of the housing container 1 for an implant fixture. Since the housing main body 2 is not in direct contact with the dental implant fixture, the housing main body 2 is made of glass or a resin.

Figure 2:
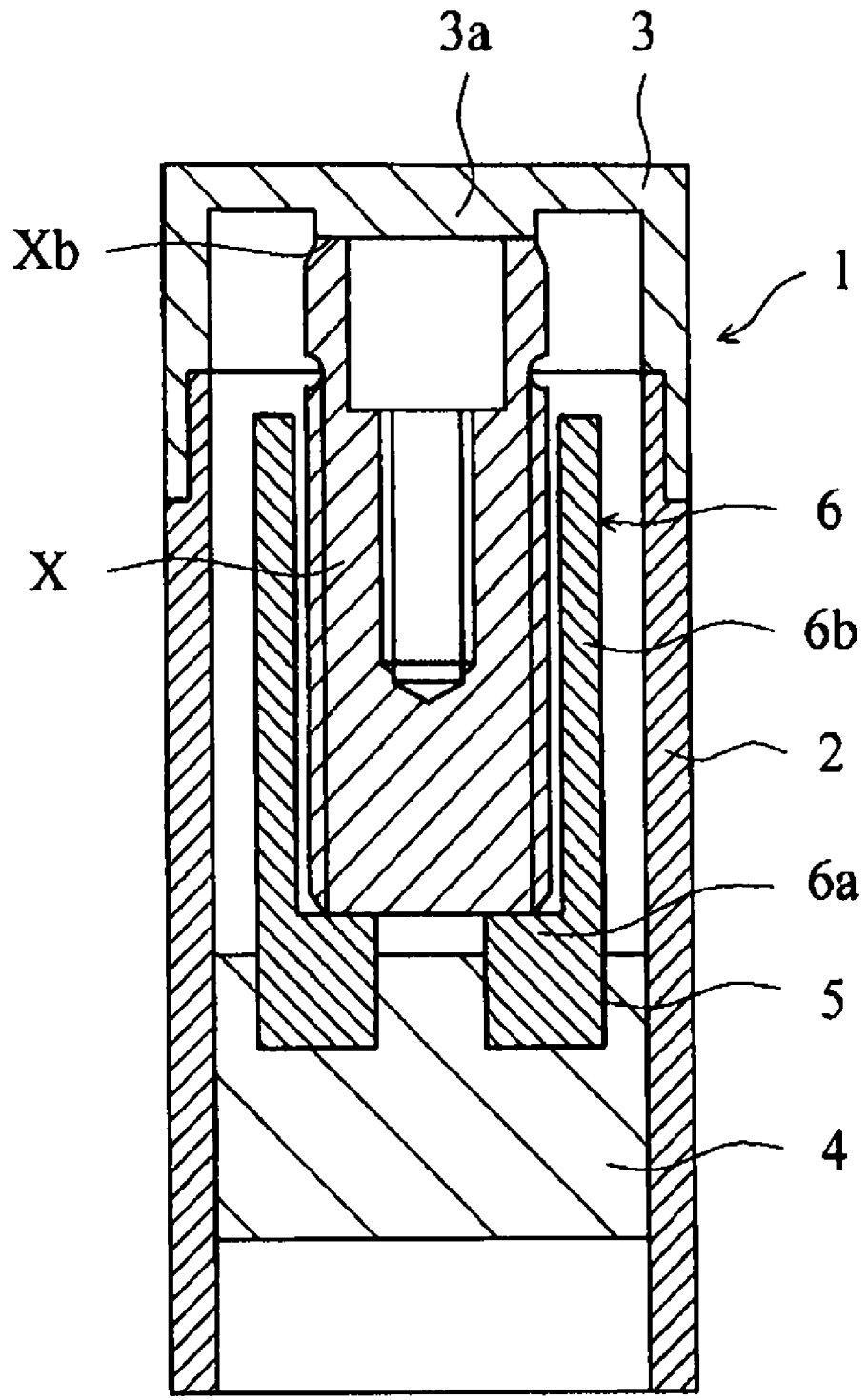
FIG. 2 is a longitudinal sectional view for illustrating another example of the housing container for an implant fixture according to the present invention.
Figure 4:
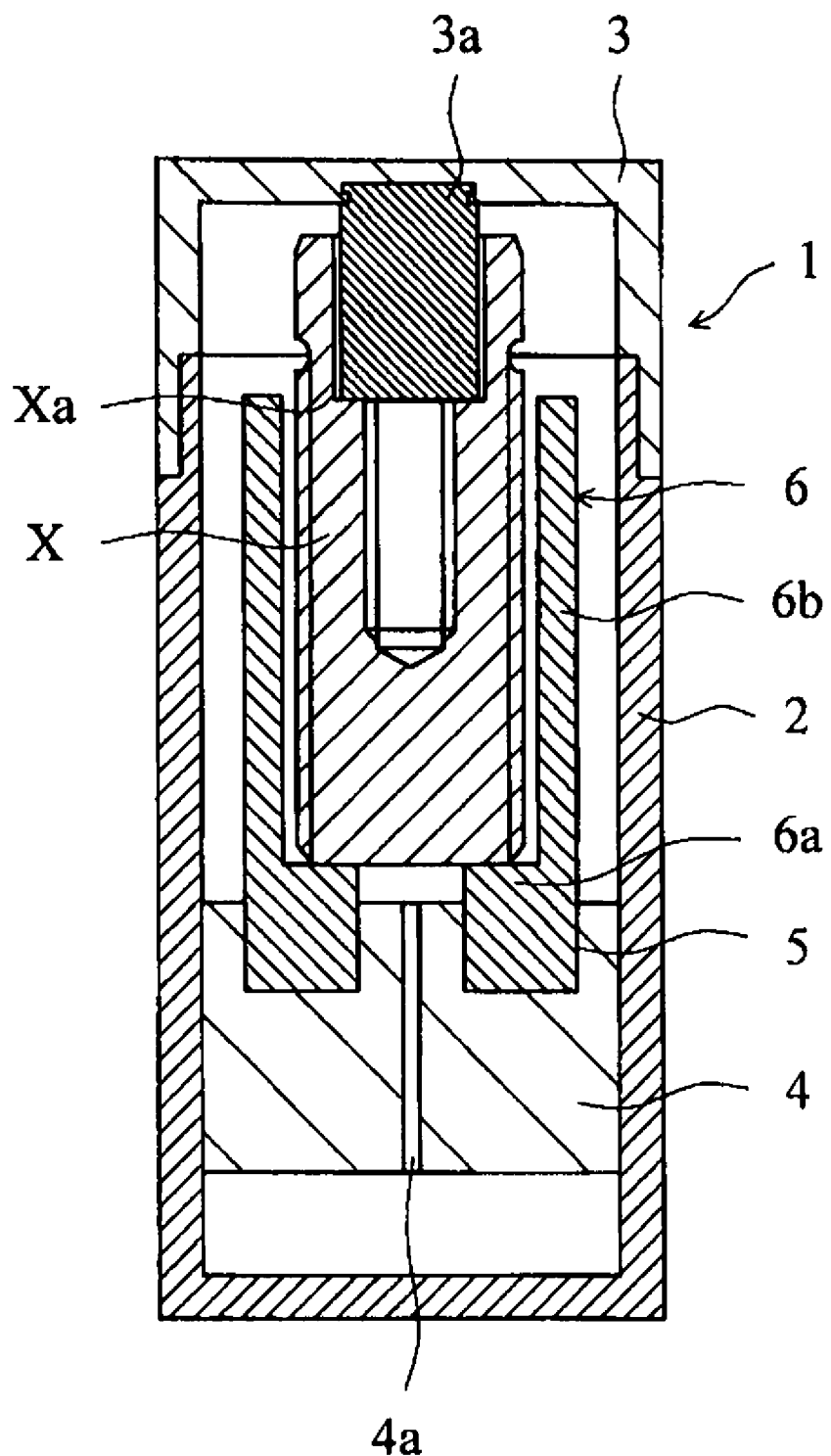
FIG. 4 is a longitudinal sectional view for illustrating one example of the housing container for an implant fixture according to the present invention, where a housing main body is formed in a container shape having a closed lower end.
Figure 5:
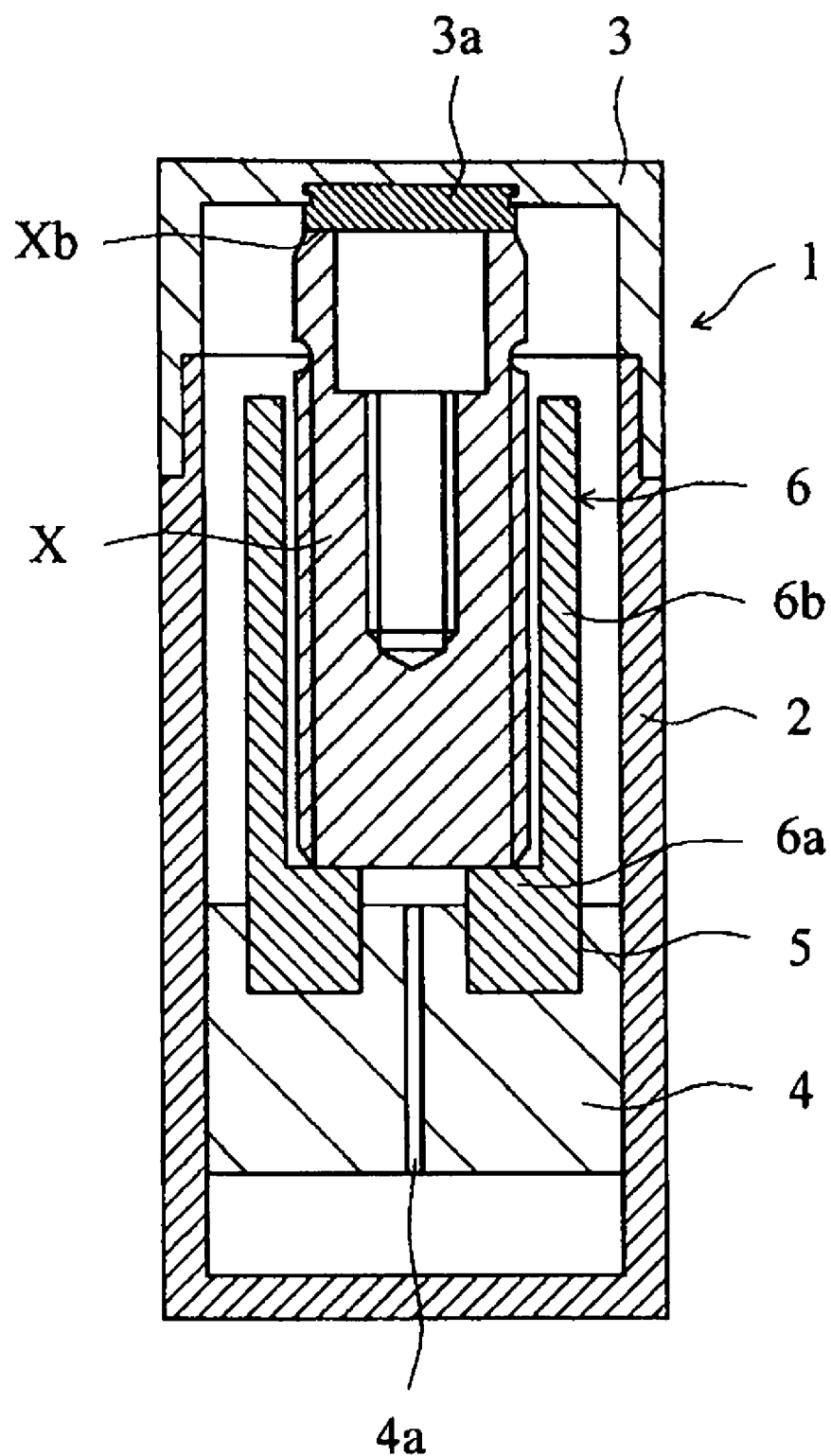
FIG. 5 is a longitudinal sectional view for illustrating another example of a housing container for an implant fixture according to the present invention, where a housing main body is formed in a container shape having a closed lower end.

The cap 3 seals an upper part of the housing main body 2 by fitting or the like. Since the cap 3 is not in direct contact with the dental implant fixture, the cap 3 is made of a resin. Further, the cap 3 includes a press part 3a at the inner surface thereof. The press part 3a is inserted into the engagement hole Xa of the dental implant fixture X so as to be in contact with the dental implant fixture X as illustrated in FIGS. 1 and 4, where the engagement hole Xa engages with a tool for embedding the dental implant fixture X into a jawbone. Or, the press part 3a is in contact with an upper surface Xb on the intraoral side of the dental implant fixture X as illustrated in FIGS. 2 and 5. Or, although the configuration is not illustrated, the press part 3a is inserted into the engagement hole Xa provided on the intraoral side of the dental implant fixture X so as to be in contact with the dental implant fixture X and is simultaneously in contact with the upper surface Xb on the intraoral side, where the engagement hole Xa engages with a tool for embedding the dental implant fixture X into a jawbone. The press part 3a positions and fixes the cap 3 on an upper part at the intraoral side of the dental implant fixture X. As illustrated in FIGS. 1, 2, 4, and 5, although the press part 3a is in direct contact with the dental implant fixture X, the contacting part is not a portion to be embedded into an alveolar ridge of the dental implant fixture X, but a portion in the engagement hole Xa for the tool for embedding the dental fixture X into a jawbone, and/or the upper surface Xb on the intraoral side. Thus, the press part 3a can be made of a resin. However, if the upper surface Xb on the intraoral side of the dental implant fixture X could be in direct contact with a jawbone, the press part 3a is preferably made of titanium or a titanium alloy. When the press part 3a is made of titanium or a titanium alloy, the press part 3a is to be inserted into the inner surface of the cap 3 and bonded. Or, several stepped parts are provided on the inner surface of the cap 3, and the press part 3a is pressed in and fitted to the inner surface, as illustrated in FIGS. 4 and 5. When the press part 3a is made of a resin, for example, the press part 3a is integrally formed with the cap 3 and is provided on the inner surface of the cap 3, as illustrated in FIGS. 1 and 2.

Figure 3:
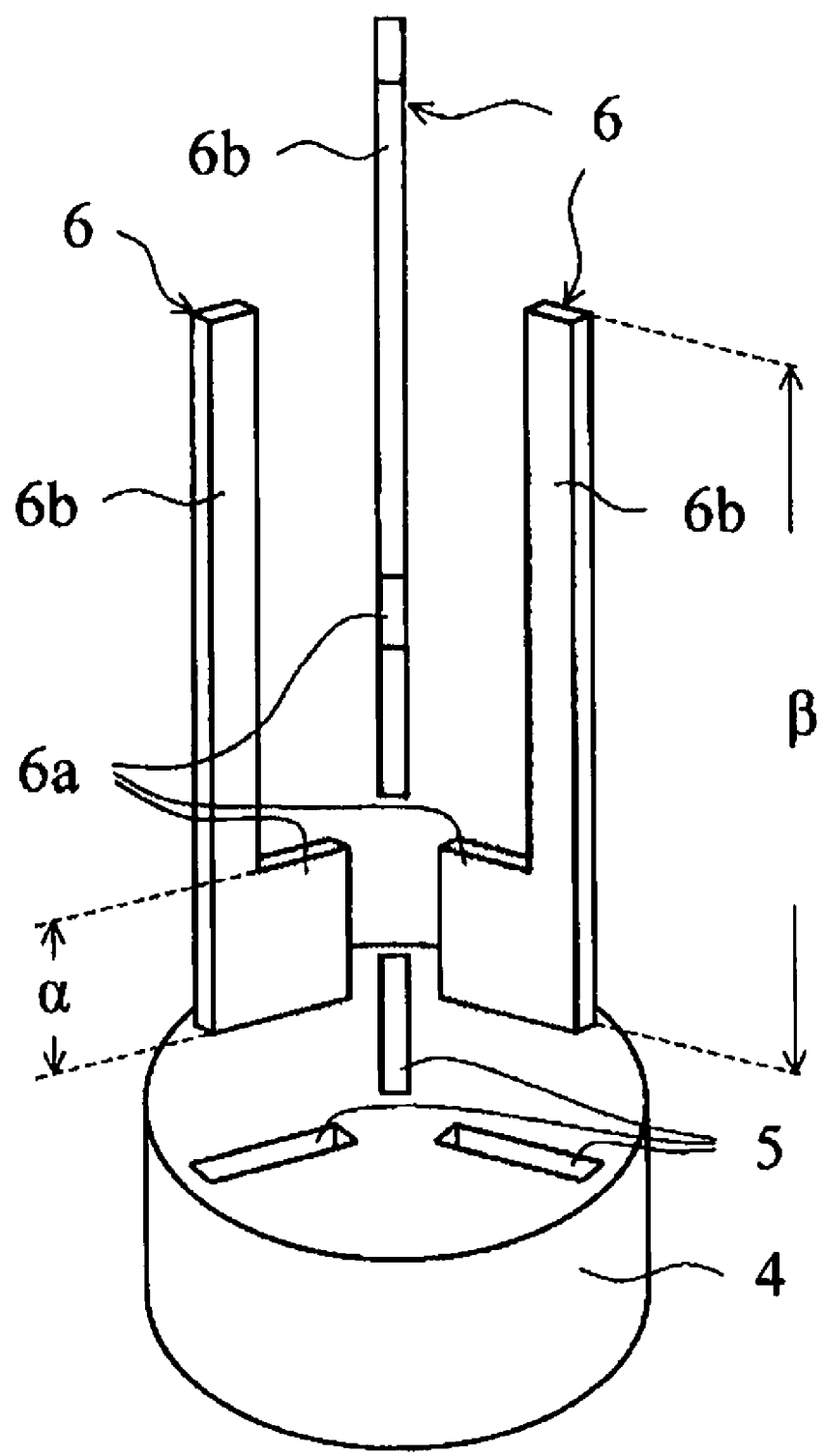
FIG. 3 is a perspective view for illustrating one example in which groove parts are formed on an implant fixture holding member and plate-like guide parts are inserted into the groove parts.

The implant fixture holding member 4 fits to the bottom part side of the housing main body 2. Since the implant fixture holding member 4 is not in direct contact with the dental implant fixture X, the implant fixture holding member 4 is made of a resin. The implant fixture holding member 4 has three or more groove parts 5 on the upper surface side thereof, and the groove parts 5 are formed radially from a part around a center to an end side of the implant fixture holding member 4. A plate-like guide part 6 made of titanium or a titanium alloy is inserted into each of the groove parts 5. The plate-like guide part 6 has, at the center side thereof, a projected portion 6a slightly projecting from an upper surface of the implant fixture holding member 4. The plate-like guide part has, at the radial end side thereof, an erected portion 6b extending up to at least equal to or more than ⅓ of a height from a tip of the dental implant fixture X and erecting around an outer peripheral surface of the dental implant fixture X. At the center side of the groove parts 5 provided on the implant fixture holding member 4, the tip at the side opposite to the intraoral side of the dental implant fixture X is positioned and fixed by the projected portions 6a of the plate-like guide parts 6 which slightly project from the upper surface of the implant fixture holding member 4. At the radial end side of the groove parts 5 provided on the implant fixture holding member 4, the dental implant fixture X is positioned and fixed by the erected portions 6b of the plate-like guide parts 6, which erect up to at least equal to or more than ⅓ of the height from the tip at the side opposite to the intraoral side of the dental implant fixture X and erect from parts around the outer peripheral surface of the dental implant fixture X. Therefore, the dental implant fixture is positioned and fixed when being housed in the housing container 1 for an implant fixture. Hence, the dental implant fixture X does not move greatly and is not damaged at a time of conveyance. For example, as illustrated in FIG. 3, the implant fixture holding member 4 having the aforementioned configuration can be produced by forming the three radial groove parts 5 from the part around the center of the upper surface of the implant fixture holding member 4, and inserting the L-shaped plate-like guide part 6 into each of the groove parts 5. In this implant fixture holding member 4, the L-shaped plate-like guide part 6 has a height α of the projected portion 6a slightly projecting from the upper surface at the center side, and has a height β of the erected portion 6b erecting at the radial end side, where the height α is larger than the depth of the groove parts 5, and the height β is equal to or larger than the total of the depth of the groove parts 5 and ⅓ of the height of the dental implant fixture X. In addition, in this implant fixture holding member 4, after deciding positions of the groove parts 5 from the part around the center to the end side according to an outer diameter and type of the dental implant fixture X to be housed and forming them, the plate-like guide part 6 can be fitted into each of the groove parts 5. Thus, the housing container 1 for an implant fixture can house various kinds of dental implant fixtures X having different outer diameters. Furthermore, when the housing main body 2 is formed in a container shape having a closed lower end, it is preferable that the implant fixture holding member 4 includes a communication hole 4a through which the upper surface side communicates with the lower surface side thereof as illustrated in FIG. 4, in order to easily fit the implant fixture holding member 4 into the bottom part side of the housing main body 2.

The housing container 1 for an implant fixture according to the present invention houses the dental implant fixture X with the housing main body 2, the cap 3, and the implant fixture holding member 4 with high sealability, where the housing main body is a base body, the cap 3 seals the upper part of the housing main body 2, and the implant fixture holding member 4 fits into the bottom part side of the housing main body 2. Thus, the dental implant fixture X can secure a sterilized condition until a time just before performing of a dental implant treatment. Further, titanium materials are used only for the plate-like guide parts 6, including the portions 6a which are in direct contact with a portion of the dental implant fixture X embedded in an alveolar ridge, and the erected portions 6b which could be in contact with a portion of the dental implant fixture embedded in the alveolar ridge residual ridge. The projected portions 6a slightly project from the upper surface of the implant fixture holding member 4. The erected portions 6b at the radial end side extend up to at least equal to or more than ⅓ of the height from the tip of the dental implant fixture and erect at parts around the outer peripheral surface of the dental implant fixture X. Thus, the housing container 1 for an implant fixture can limit the use of titanium or a titanium alloy to the minimum, and can thus prevent wasting of titanium resources. Further, the press part 3a provided at the inner surface of the cap 3 is inserted into the engagement hole Xa to fix the dental implant fixture X, and/or is in contact with the upper surface Xb on the intraoral side to fix the upper part of the dental implant fixture, where the engagement hole Xa is provided on the intraoral side of the dental implant fixture to engage with the tool for embedding the dental implant fixture into a jawbone. Further, the plate-like guide parts 6 made of titanium or a titanium alloy is inserted into the groove parts 5 which are formed according to an outer diameter and a type of the dental implant fixture X to be housed. The plate-like guide parts 6 include the projected portions 6a which are located at the center side thereof and slightly project from the upper surface of the implant fixture holding member 4. The projected portions 6a are in contact with the tip at the side opposite to the intraoral side of the dental implant fixture X, and fix the lower part of the dental implant fixture X. Therefore, since the dental implant fixture X is held by the press part 3a and the projected portions 6a to be positioned and fixed, various dental implant fixtures having different outer diameters or types can be accurately and easily positioned and fixed. Further, the plate-like guide parts 6 include the erected portions 6b at the radial end part side. The erected portions 6b extend up to at least equal to or more than ⅓ of the height from the tip of the dental implant fixture X, and erect at the parts around the outer peripheral surface of the dental implant fixture X. Therefore, since the erected portions 6b erect along the outer surface of the dental implant fixture X, the fixed dental implant fixture X does not move greatly and is not damaged even when a big impact is applied during conveyance. Furthermore, in the housing container 1 for an implant fixture having the aforementioned configuration, a user can easily take out the dental implant fixture X by directly engaging the tool for embedding the dental implant fixture X into a jawbone with the engagement hole Xa on the intraoral side of the dental implant fixture X after opening the housing container 1 for an implant fixture. When the dental implant fixture X is taken out, the dental implant fixture X is not damaged because of being not scratched with the housing container 1 for an implant fixture.

In the housing container 1 for an implant fixture according to the present invention, when the housing main body 2 is formed in a cylindrical shape having an open upper end and an open lower end, the housing main body 2 can house various kinds of dental implant fixtures X having different lengths by fitting the implant fixture holding member 4 into the housing main body 2 according to the length of the dental implant fixture X to be housed. So, it is preferable. Further, when the housing main body 2 is formed in a container shape having a closed lower end instead of the cylindrical shape, the housing container 1 for an implant fixture can have higher sealability, so it is preferable.

Figure 6:
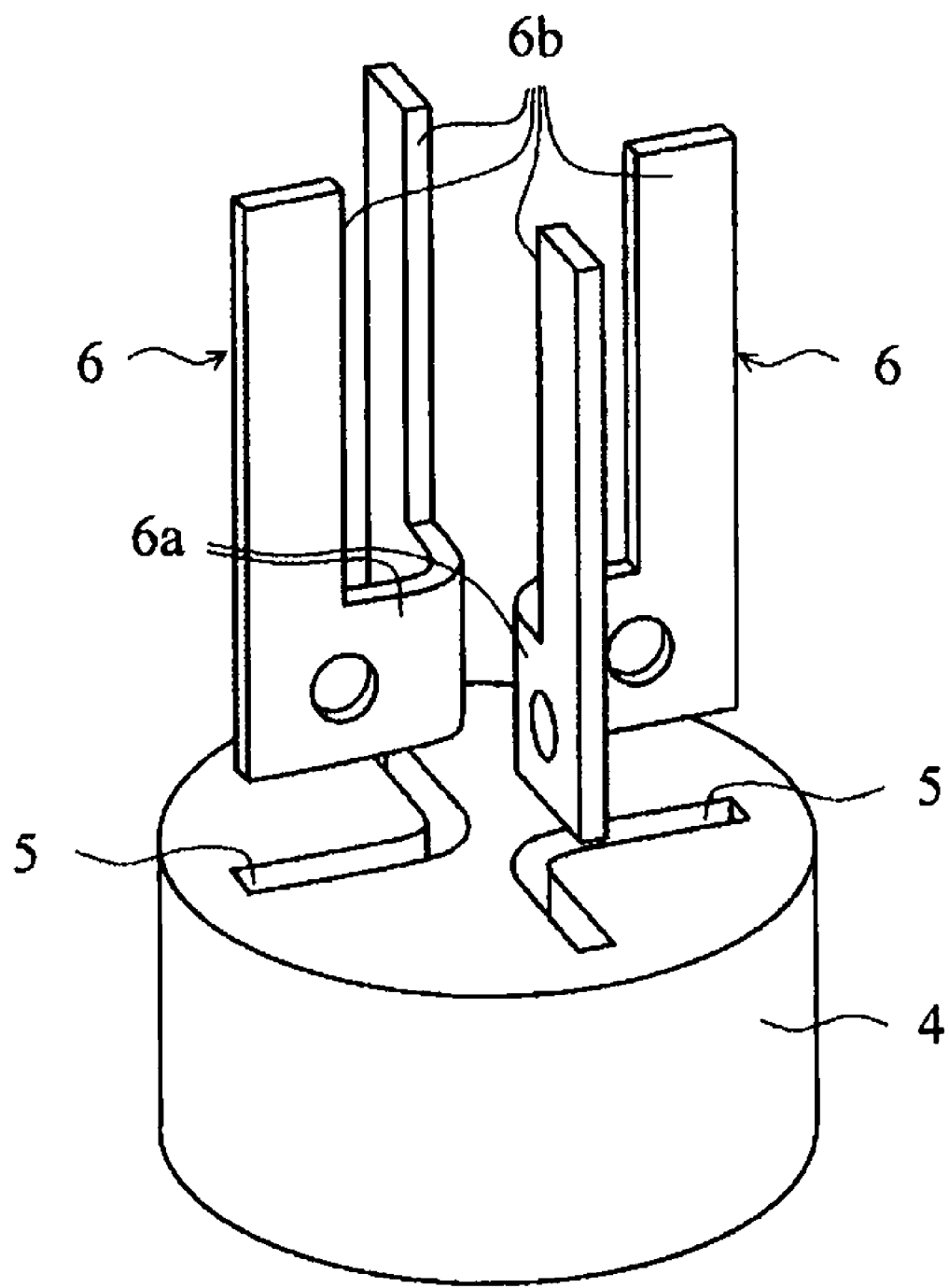
FIG. 6 is a perspective view for illustrating one example in which an implant fixture holding member has at least two adjacent groove parts communicating with each other at the radial center sides to form a V shape, and a plate-like guide part inserted into the groove parts is U shape and an opening side of the plate like guide part is upward, a bottom part of the plate like guide part being the opposite side to the opening side is bent in a V shape at a center part thereof.
Figure 7A:
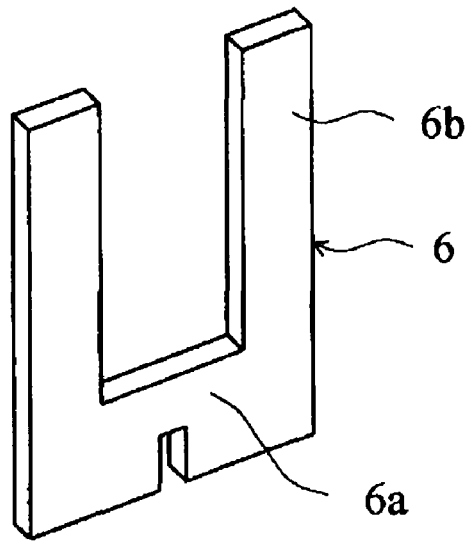
FIGS. 7(A)-7(C) are perspective views for illustrating one example in which a groove part is formed in a cross shape intersecting at a center axis on the upper surface side of the implant fixture holding member, and plate-like guide parts having a U shape are arranged so as to intersect with each other by a halving joint and inserted into the groove parts.
Figure 7B:
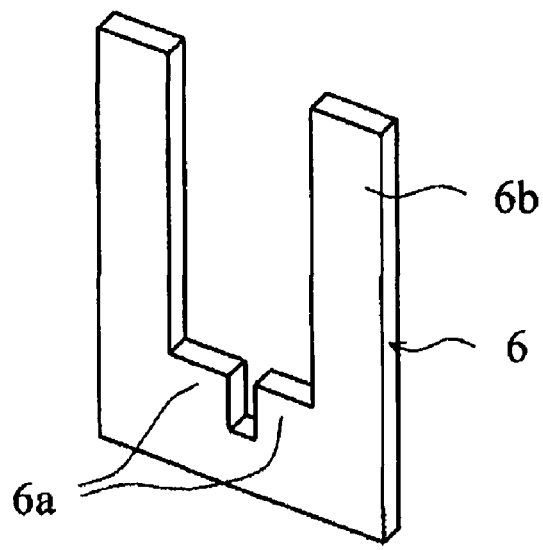
Figure 7C:
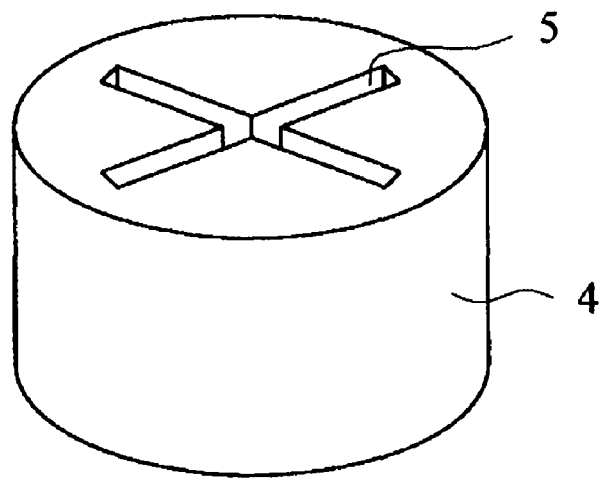

The housing container 1 for an implant fixture can also have the configuration that at least two adjacent groove parts among the groove parts 5 are formed on the upper surface of the implant fixture holding member 4 so as to communicate with each other at the radial center sides to form a V shape, as illustrated in FIG. 6, the plate-like guide part 6 inserted into the groove parts 5 is U shape and an opening side of the plate-like guide part is upward, a bottom part of the plate like guide part being opposite side to the opening side is bent in a V shape at a center part thereof plate-like guide part 6 is. Further, the housing container 1 for an implant fixture can also have the configuration that the groove part 5 is formed in a cross shape intersecting at a center axis on the upper surface side of the implant fixture holding member 4, and the plate-like guide parts 6 having a U shape are arranged so as to intersect with each other by a halving joint and inserted into the groove part 5. According to these configurations, since the number of the plate-like guide parts 6 to be inserted into the groove parts 5 can be reduced, an operation for inserting the plate-like guide parts 6 into the groove parts 5 can be made easy, so it is preferable.

What is claimed is:

1. A housing container for an implant fixture comprising:
a housing main body made of glass or a resin to house a dental implant fixture having an engagement hole in the intraoral side for engagement with a tool for embedding the dental implant fixture into a jawbone;
a cap made of a resin to seal an upper part of the housing main body and provided with a press part at an inner surface, the press part being inserted into the engagement hole of the dental implant fixture to be in contact with the dental implant fixture, and/or being in contact with an upper surface on the intraoral side of the dental implant fixture; and
an implant fixture holding member made of a resin and fitted into the bottom part side in the housing main body,
wherein the implant fixture holding member has three or more groove parts on the upper surface side thereof, the groove parts are formed radially from a part around a center to an end side of the implant fixture holding member, a plate-like guide part made of titanium or a titanium alloy is inserted into each of the groove parts, the plate-like guide part has, at the center side thereof, a projected portion slightly projecting from the upper surface of the implant fixture holding member, and
the plate-like guide part has, at the radial end side thereof, an erected portion extending up to at least equal to or more than ⅓ of a height from a tip of the dental implant fixture, and erecting around an outer peripheral surface of the dental implant fixture.

2. The housing container for an implant fixture as claimed in claim 1,
wherein the housing main body is formed in a cylindrical shape having an open upper end and an open lower end.

3. The housing container for an implant fixture as claimed in claim 1,
wherein the housing main body is formed in a container shape having a closed lower end.

4. The housing container for an implant fixture as claimed in claim 1,
wherein at least two adjacent groove parts communicate with each other at the radial center sides to form a V shape, and the plate-like guide part inserted into the groove parts is U shape and an opening side of the plate-like guide part is upward, a bottom part of the plate-like guide part being the opposite side to the opening side is bent in a V shape at a center part thereof.

5. The housing container for an implant fixture as claimed in claim 2,
wherein at least two adjacent groove parts communicate with each other at the radial center sides to form a V shape, and the plate-like guide part inserted into the groove parts is U shape and an opening side of the plate-like guide part is upward, a bottom part of the plate-like guide part being the opposite side to the opening side is bent in a V shape at a center part thereof.

6. The housing container for an implant fixture as claimed in claim 3,
wherein at least two adjacent groove parts communicate with each other at the radial center sides to form a V shape, and the plate-like guide part inserted into the groove parts is U shape and an opening side of the plate-like guide part is upward, a bottom part of the plate-like guide part being the opposite side to the opening side is bent in a V shape at a center part thereof.

7. The housing container for an implant fixture as claimed in claim 1,
wherein the groove part is formed in a cross shape intersecting at a center axis on the upper surface side of the implant fixture holding member, and the plate-like guide parts having a U shape are arranged so as to intersect with each other by a halving joint and inserted into the groove parts.

8. The housing container for an implant fixture as claimed in claim 2,
wherein the groove part is formed in a cross shape intersecting at a center axis on the upper surface side of the implant fixture holding member, and the plate-like guide parts having a U shape are arranged so as to intersect with each other by a halving joint and inserted into the groove parts.

9. The housing container for an implant fixture as claimed in claim 3,
wherein the groove part is formed in a cross shape intersecting at a center axis on the upper surface side of the implant fixture holding member, and the plate-like guide parts having a U shape are arranged so as to intersect with each other by a halving joint and inserted into the groove parts.

* * * * *